(12) United States Patent
Orbay

(10) Patent No.: US 6,358,250 B1
(45) Date of Patent: Mar. 19, 2002

(54) VOLAR FIXATION SYSTEM

(75) Inventor: Jorge L. Orbay, Miami, FL (US)

(73) Assignee: Hand Innovations, Inc., Miami, FL (US)

( * ) Notice: Subject to any disclaimer, the term of this patent is extended or adjusted under 35 U.S.C. 154(b) by 0 days.

(21) Appl. No.: 09/495,854

(22) Filed: Feb. 1, 2000

(51) Int. Cl.$^7$ ............................................. A61B 17/80
(52) U.S. Cl. ....................................................... 606/69
(58) Field of Search ............................ 606/60, 69, 70, 606/71; 623/21.12

(56) References Cited

U.S. PATENT DOCUMENTS

| | | | | |
|---|---|---|---|---|
| 2,500,370 A | * | 3/1950 | McKibbin | 606/67 |
| 3,741,205 A | * | 6/1973 | Markolf et al. | 606/61 |
| 5,015,248 A | * | 5/1991 | Burstein et al. | 606/74 |
| 5,304,180 A | * | 4/1994 | Slocum | 606/69 |
| 5,437,667 A | * | 8/1995 | Papierski et al. | 606/55 |
| 6,096,040 A | * | 8/2000 | Esser | 606/69 |
| 6,183,475 B1 | * | 2/2001 | Lester et al. | 606/69 |
| 6,197,028 B1 | * | 3/2001 | Ray et al. | 606/61 |
| 6,221,073 B1 | * | 4/2001 | Weiss et al. | 606/60 |

* cited by examiner

Primary Examiner—Gene Mancene
Assistant Examiner—Michael B. Priddy
(74) Attorney, Agent, or Firm—David P. Gordon; David S Jacobson; Thomas A Gallagher

(57) ABSTRACT

A volar fixation system includes a T-shaped plate intended to be positioned against the volar side of the radial bone, a plurality of bone screws for securing the plate along an non-fractured portion of the radial bone, and a plurality of bone pegs which extend from the plate and into bone fragments of a Colles' fracture. The plate is a T-shaped plate including a plurality of screw holes and a plurality of threaded peg holes. According to a first preferred aspect of the invention, the peg holes are preferably non-linearly arranged and provided such that the holes are positioned increasingly distal in a medial to lateral direction along the second side. According to a second preferred aspect, axes through the holes are oblique relative to each other and preferably angled relative to each other in two dimensions. The system includes a guide plate which temporarily sits on top of the volar plate and includes holes oriented according to the axes of the peg holes for guiding a drill into the bone fragments at the required orientation. The volar plate is positioned against the radius and screws are inserted through the screw holes to secure the volar plate to the radius. The bone fragments are aligned, and the guide plate assists in drilling pilot hole. The pegs are inserted through the peg holes and into the drilled holes in the bone. The volar fixation system thereby secures the bone fragments in their proper orientation.

13 Claims, 3 Drawing Sheets

VOLAR FIXATION SYSTEM

BACKGROUND OF THE INVENTION

1. Field of the Invention

This invention relates broadly to surgical devices. More particularly, this invention relates to a bone fixation system, and particularly to a fixation system adapted to fixate a Colles' (or distal radial) fracture.

2. State of the Art

Referring to FIG. 1, a Colles' fracture is a fracture resulting from compressive forces being placed on the distal radius 10, and which causes backward displacement of the distal fragment 12 and radial deviation of the hand at the wrist 14. Often, a Colles' fracture will result in multiple bone fragments 16, 18, 20 which are movable and out of alignment relative to each other. If not properly treated, such fractures result in permanent wrist deformity. It is therefore important to align the fracture and fixate the bones relative to each other so that proper healing may occur.

Alignment and fixation are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time consuming procedure. Moreover, unless the bracing is quite complex, the fracture may not be properly stabilized. Plating utilizes a stabilizing metal plate typically against the dorsal side of the bones, and a set of parallel pins extending from the plate into the holes drilled in the bone fragments to provide stabilized fixation of the fragments. However, the currently available plate systems fail to provide desirable alignment and stabilization.

SUMMARY OF THE INVENTION

It is therefore an object of the invention to provide an improved fixation and alignment system for a Colles' fracture.

It is another object of the invention to provide a volar fixation system which desirably aligns and stabilizes multiple bone fragments in a distal radial fracture to permit proper healing.

In accord with these objects, which will be discussed in detail below, a volar fixation system is provided which generally includes a T-shaped plate intended to be positioned against the volar side of the radial bone, a plurality of bone screws for securing the plate along a non-fractured portion of the radial bone, and a plurality of bone pegs which extend from the plate and into bone fragments of a Colles' fracture.

The plate is generally a T-shaped plate defining an elongate body, a head portion angled relative to the body, a first side which is intended to contact the bone, and a second side opposite the first side. The body portion includes a plurality of countersunk screw holes for the extension of the bone screws therethrough. The head portion includes a plurality of threaded peg holes for receiving the pegs therethrough. According to a first preferred aspect of the invention, the peg holes are preferably non-linearly arranged and provided such that the holes are positioned increasingly distal in a medial to lateral direction along the second side. In addition, according to a second preferred aspect of the invention, axes through the holes are oblique relative to each other, and are preferably angled relative to each other in two dimensions. The pegs having a threaded head and a relatively smooth cylindrical shaft.

The system preferably also includes a guide plate which temporarily sits on top of the volar plate and includes holes oriented according to the axes of the peg holes for guiding a drill into the bone fragments at the required orientation. The volar plate and guide plate are also preferably provided with mating elements to temporarily stabilize the guide plate on the volar plate during the hole drilling process.

In use, the volar plate is positioned with its first side against the volar side of the radius and bone screws are inserted through the bone screw holes into the radius to secure the volar plate to the radius. The bone fragments are then aligned and the guide plate is positioned on the second side of the volar plate. A drill, guided by guide holes in the guide plate, drills holes into the bone fragments, and the guide plate is then removed.

The pegs are then inserted through the peg holes and into the holes in the bone, and the heads of the pegs are threadably engaged in the volar plate. The volar fixation system thereby secures the bone fragments in their proper orientation.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
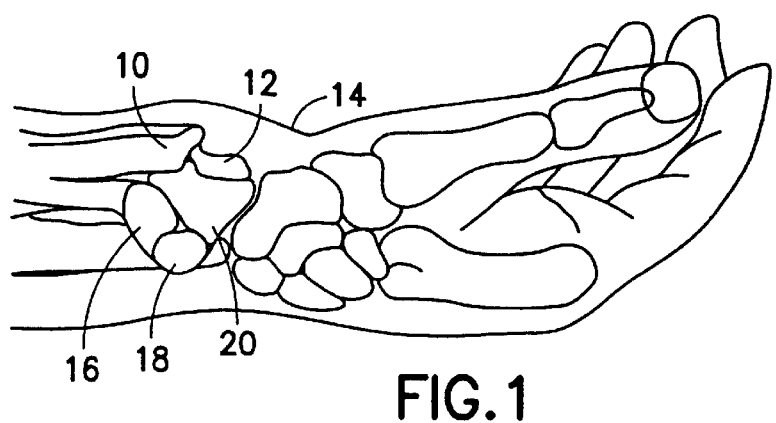
FIG. 1 is an illustration of an extremity subject to a Colles' fracture.
Figure 2:
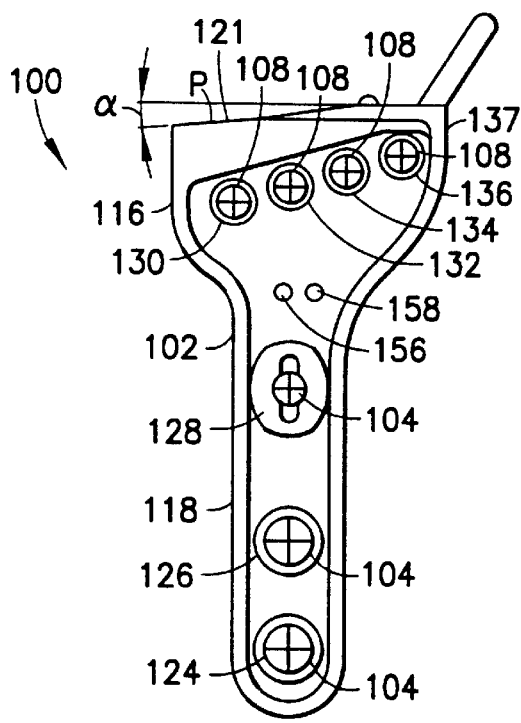
FIG. 2 is a top volar view of the volar fixation system of the invention.
Figure 3:
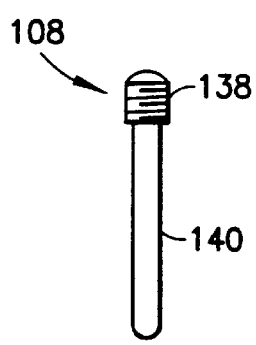
FIG. 3 is a side view of a bone peg of the volar fixation system of the invention.
Figure 4:
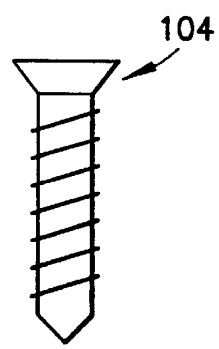
FIG. 4 is a side view of a bone screw of the volar fixation system of the invention.

Turning now to FIGS. 2 through 4, a volar fixation system 100 for aligning and stabilizing multiple bone fragments in a Colles' fracture generally includes a substantially rigid T-shaped plate 102 intended to be positioned against the volar side of the radial bone, a plurality of bone screws 104 for securing the plate 102 along a non-fractured portion of the radial bone, and a plurality of bone pegs 108 which extend from the plate 102 and into bone fragments of a Colles' fracture.

Figure 5:
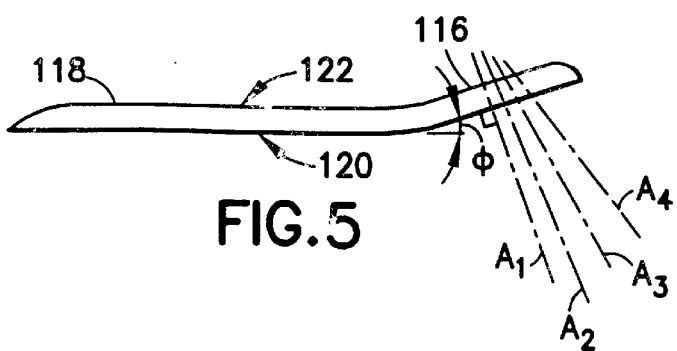
FIG. 5 is a side view of the volar plate of the volar fixation system of the invention.
Figure 6:
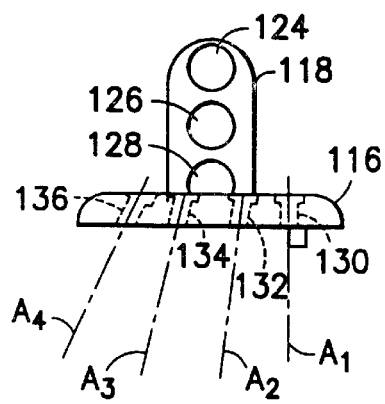
FIG. 6 is a front end view of the volar plate of the volar fixation system of the invention.

Referring to FIGS. 2, 5 and 6, more particularly, the T-shaped plate 102 defines a head portion 116, an elongate body portion 118 angled relative to the head portion, a first side 120 which is intended to contact the bone, and a second side 122 opposite the first side. The first side 120 at the head portion is preferably planar, as is the first side at the body portion. As the head portion and body portion are angled relative to each other, the first side preferably defines two planar portions. The angle $\phi$ between the head portion 116 and the body portion 118 is preferably approximately 18° and bent at a radius of approximately 1.00 inch (FIG. 5). The distal edge 121 of the head portion 116 is preferably angled proximally toward the medial side at an angle $\alpha$, e.g., 5°, relative to a line P, which is perpendicular to the body portion. The head portion 116 preferably has a width of 0.913 inch and a greatest proximal-distal dimension (i.e., from the corner of angle $\alpha$ to the body portion) of approximately 0.69 inch, and the body portion preferably has a width of 0.375 inch and a length of 1.40 inches. The plate 102 preferably has a thickness of approximately 0.098 inch. The plate 102 is preferably made from a titanium alloy, such as Ti-6A-4V.

The body portion 118 includes three preferably countersunk screw holes 124, 126, 128 for the extension of the bone screws 104 therethrough. The first screw hole 124 has a center preferably 0.235 inch from the end of the body portion, the second screw hole 126 has a center preferably 0.630 inch from the end of the body portion, and the third screw hole 128 is preferably generally elliptical (or oval) and defines foci-like locations at 1.020 inches and 1.050 inches from the end of the body portion. The head portion 116 includes four threaded peg holes 130, 132, 134, 136 for individually receiving the pegs 108 therethrough. According to a first preferred aspect of the invention, the peg holes 130, 132, 134, 136, preferably 0.100 inch in diameter, are preferably non-linearly arranged along the head portion 116, and are provided such that the adjacent peg holes are provided further distally in a medial to lateral direction along the second side. More particularly, according to a preferred embodiment of the invention, the center of peg hole 130 is located 0.321 inch proximal line P and 0.719 inch medial of the lateral edge 137 of the head portion, the center of peg hole 132 is located 0.296 inch proximal line P and 0.544 inch medial of the lateral edge 137, the center of peg hole 134 is located 0.250 inch proximal line P and 0.369 inch medial of the lateral edge 137, and the center of peg hole 136 is located 0.191 inch proximal line P and 0.194 inch medial of the lateral edge 137.

In addition, according to a second preferred aspect of the invention, the peg holes define axes $A_1$, $A_2$, $A_3$, $A_4$ which are oblique (not parallel) relative to each other, and more preferably are angled in two dimensions (medial/lateral and proximal/distal) relative to each other; i.e., the pegs once inserted into the peg holes are also angled in two dimensions relative to each other. More particularly, the first axis $A_1$ of the first peg hole 130 (that is, the most proximal and medial peg hole) is preferably directed normal to the first side 120 of the head portion 116. The axis $A_2$ of the adjacent peg hole 132, i.e., the second axis, is preferably angled 5° distal and 7.5° lateral relative to the first axis $A_1$. The axis $A_3$ of the peg hole 134 laterally adjacent the second peg hole 132, i.e., the third axis, is preferably angled 10° distal and 15° lateral relative to the first axis $A_1$. The axis $A_4$ of the peg hole 134 laterally adjacent the third peg hole 132, i.e., the fourth axis, is preferably angled 20° distal and 20° lateral relative to the first axis $A_1$. The second side of the head portion 116, distal of the peg holes 130, 132, 134, 136 is preferably beveled.

Referring back to FIG. 3, the pegs 108, preferably approximately 0.872 inch in length, each have a threaded head 138 adapted to threadably engage the threads about the peg holes 130, 132, 134, 136, and have a relatively smooth non-threaded cylindrical shaft 140. The shafts 140 are preferably approximately 0.0675 inch in diameter and 0.765 inch in length. Such dimensions permit the pegs to adequately support the bone fragments such that the bone is able to heal correctly. The pegs 108 are also preferably made from titanium alloy, and may be coated in a ceramic, e.g., titanium nitride, to provide a bone interface which will not adversely affect bone healing.

Figure 7:
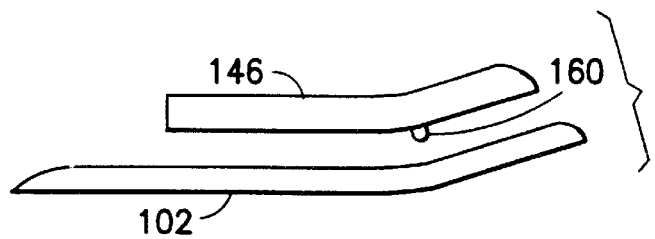
FIG. 7 is an exploded side view of the volar plate and guide plate of the fixation system of the invention.
Figure 8:
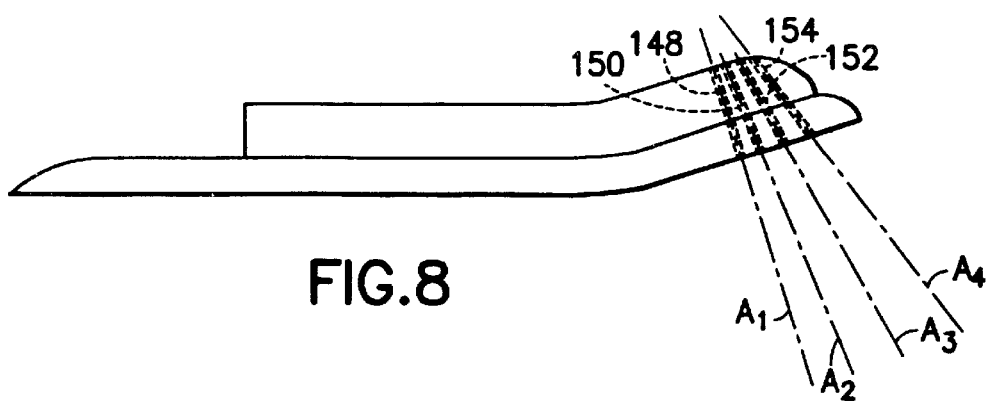
FIG. 8 is a side view of the guide plate positioned on the volar plate to provide drill guide paths in accord with the invention.
Figure 9:
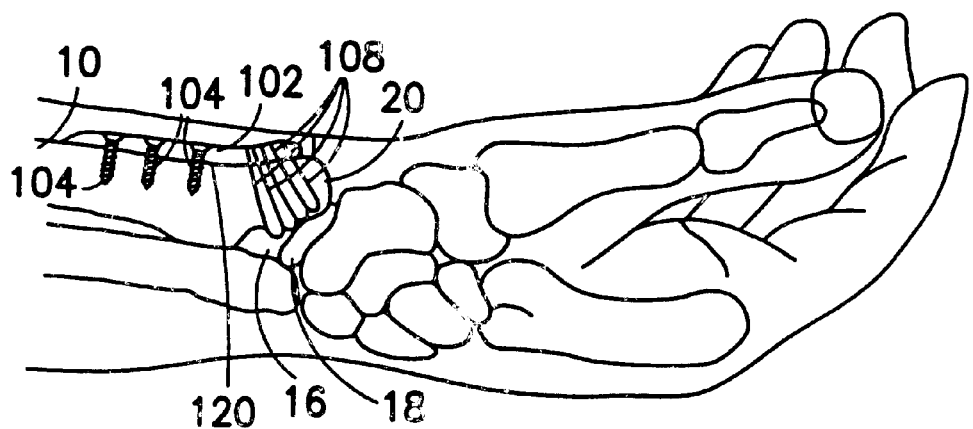
FIG. 9 is an illustration of the volar fixation system provided in situ aligning and stabilizing a Colles' fracture.

Turning now to FIGS. 7 and 8, the system 100 preferably also includes a guide plate 146 which temporarily sits on the second side 122 of the volar plate 102 and includes guide holes 148, 150, 152, 154 (illustrated in overlapping section in FIG. 8) oriented according to the axes $A_1$, $A_2$, $A_3$, $A_4$ of the peg holes for guiding a drill into the bone fragments at the required orientation. That is, the guide holes together with the peg holes define a drill guide path along the axes with sufficient depth to accurately guide a drill (not shown) to drill holes at the desired pin orientations. The volar plate 102 and guide plate 146 are also preferably provided with mating elements, such as a plurality of holes 156, 158 on the second side of the volar plate (FIG. 2), and a plurality of protuberances 160 on the mating side of the guide plate (FIG. 7), to temporarily stabilize the guide plate on the volar plate during the hole drilling process.

Referring to FIGS. 2 through 9, in use, the volar plate 102 is positioned with its first side 120 against the volar side of the radius. Bone screws 104 (either self-tapping or inserted with the aid of pre-drilled pilot holes) are inserted through the bone screw holes 124, 126, 128 into the radius bone 10 to secure the volar plate 102 to the radius. The bone fragments 16, 18, 20 are then aligned with the radius 10. Next, the guide plate 146 is positioned on the second side of the volar plate. A drill, guided by a guide path formed by the peg holes and the guide holes, drills holes into and between the bone fragments 16, 18, 20 (and possibly also a portion of the integral radius, depending upon the particular location and extent of the fracture), and the guide plate is then removed. The pegs 108 are then inserted through the peg holes 130, 132, 134, 136 and into the holes drilled into the fragments, and the heads of the pegs are threadably engaged in the volar plate. The pegs 108 extending through the oblique-axis peg holes 130, 132, 134, 136 are positioned immediately below the subcondylar bone of the radius and support the bone fragments for proper healing. The volar fixation system thereby secures the bone fragments in their proper orientation.

There have been described and illustrated herein an embodiment of a volar fixation system and a method of aligning and stabilizing a Colles' fracture. While a particular embodiment of the invention have been described, it is not intended that the invention be limited thereto, as it is intended that the invention be as broad in scope as the art will allow and that the specification be read likewise. Thus, while particular materials for the elements of the system have been disclosed, it will be appreciated that other materials may be used as well. In addition, while a particular number of screw holes in the volar plate and bone screws have been described, it will be understood another number of screw holes and screws may be provided. Further, fewer screws than the number of screw holes may be used to secure to the volar plate to the radius. Also, fewer or more peg holes and bone pegs may be used, preferably such that at least two pegs angled in two dimensions relative to each other are provided. In addition, while a particular preferred angle between the head portion and body portion has been disclosed, other angles can also be used. Furthermore, while particular distances are disclosed between the peg holes and line P, it will be appreciated that the peg holes may be provided at other distances relative thereto. Moreover, while particular preferred medial/lateral and proximal/distal angles for the peg hole axes has been disclosed, it will be appreciated that yet other angles may be used in accord with the invention. It will therefore be appreciated by those skilled in the art that yet other modifications could be made to the provided invention without deviating from its spirit and scope as claimed.

What is claimed is:

1. A volar fixation plate, comprising:

a substantially rigid plate including a distal head portion and a proximal body portion angled relative to said head portion, said head portion defining a plurality of threaded peg holes adapted to individually receive fixation pegs therein, said peg holes defining a plurality of axes at least two of which are oblique relative to each other, and said body portion including at least one screw hole.

2. A volar fixation plate according to claim 1, wherein: each of said at least two axes is oblique in two dimensions relative to another of-said at least two axes.

3. A volar fixation plate according to claim 1, wherein: said head portion defines a medial side and a lateral side, and said peg holes are arranged in a generally medial to lateral direction wherein successive lateral peg holes are situated distally relative to adjacent peg holes.

4. A volar fixation plate according to claim 1, wherein: said head portion includes exactly four peg holes.

5. A volar fixation plate according to claim 4, wherein: said head portion including a lower surface, and a first of said plurality of peg holes defines a first axis of said plurality of axes directed normal to said lower surface, a second of said plurality of peg holes defines a second axis of said plurality of axes angled approximately 5° distal and 7.5° lateral relative to the first axis, a third of said plurality of peg holes defines a third axis of said plurality of axes angled approximately 10° distal and 15° lateral relative to the first axis, and a fourth of said plurality of peg holes defines a fourth axis of said plurality of axes angled approximately 20° distal and 20° lateral relative to the first axis.

6. A volar fixation plate according to claim 5, wherein: said first peg hole is most medial, said second peg hole is laterally adjacent said first peg hole, said third peg hole is laterally adjacent said second peg hole, and said fourth peg hole is laterally adjacent said third peg hole.

7. A volar fixation plate according to claim 1, wherein: said head portion is angled approximately 18° relative to said body portion.

8. A volar fixation plate according to claim 1, wherein: said head portion and said body portion are provided in a substantially T-shaped configuration relative to each other, with said body portion intersecting said head portion.

9. A volar fixation plate according to claim 1, wherein: said volar plate is made from a titanium alloy.

10. A method of aligning and stabilizing a Colles' fracture of the radius bone at the wrist, the radius bone having a volar side and a dorsal side, and the fracture including at least one bone fragment, said method comprising:

a) providing a rigid substantially T-shaped plate having a head portion and a body portion intersecting said head portion, said head portion including a plurality of threaded peg holes defining a plurality of axes, at least two of said plurality of axes being oblique in two dimensions relative to another of said at least two axes, and said body portion including a plurality of screw holes;

b) positioning said plate against the volar side of the radius bone;

c) inserting at least one bone screw through at least one of said plurality of screw holes to secure said volar plate to the radius;

d) aligning said at least one bone fragment with the radius;

e) drilling holes through said plurality of peg holes into said at least one fragment;

f) providing a plurality of pegs having an externally threaded head and an elongate shaft; and g) inserting said pegs through said peg holes and into the drilled holes and threadably securing said threaded heads in said peg holes.

11. A method according to claim 10, wherein:

each of said at least two axes is oblique in two dimensions relative to another of said at least two axes.

12. A method according to claim 10, further comprising:

h) prior to drilling holes, providing and positioning a guide plate on said volar plate, said guide plate having guide holes which when aligned with said peg holes on said volar plate define a guide path for drilling.

13. A method according to claim 12, further comprising:

i) after drilling holes, removing said guide plate.

* * * * *